(12) United States Patent
Hatahori et al.

(10) Patent No.: US 10,267,618 B2
(45) Date of Patent: Apr. 23, 2019

(54) DEFECT DETECTION METHOD AND DEFECT DETECTION APPARATUS

(71) Applicant: SHIMADZU CORPORATION, Kyoto-shi, Kyoto (JP)

(72) Inventors: Takahide Hatahori, Osaka (JP); Kenji Takubo, Uji (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/611,254

(22) Filed: Jun. 1, 2017

(65) Prior Publication Data

US 2017/0350690 A1    Dec. 7, 2017

(30) Foreign Application Priority Data

Jun. 2, 2016 (JP) .................................. 2016-111302

(51) Int. Cl.
*G01B 9/02* (2006.01)
*G01M 5/00* (2006.01)
(Continued)

(52) U.S. Cl.
CPC ..... *G01B 9/02095* (2013.01); *G01B 9/02096* (2013.01); *G01B 9/02098* (2013.01);
(Continued)

(58) Field of Classification Search
CPC ............... G01B 9/02095; G01N 29/00; G01N 21/8806; G01N 21/1702;
(Continued)

(56) References Cited

U.S. PATENT DOCUMENTS 4,567,769 A    2/1986  Barkhoudarian
4,581,939 A *  4/1986  Takahashi .......... G01N 29/2418
                                                          356/432

(Continued)

FOREIGN PATENT DOCUMENTS

| CN | 107462581 A | 12/2017 |
|----|-------------|---------|
| JP | 2004-101189 A | 4/2004 |
| JP | 2017219318 A | 12/2017 |

OTHER PUBLICATIONS

English Machine Translation of JP 2004-101189 Hitachi, Apr. 2, 2004.*

(Continued)

*Primary Examiner* — Dominic J Bologna
(74) *Attorney, Agent, or Firm* — Sughrue Mion, PLLC

(57) ABSTRACT

A defect detection apparatus is provided that can inspect a measurement region of a target object at one time and without inconsistencies arising within the measurement region. A defect detection apparatus 10 includes: a generation unit (signal generator 11 and vibrator 12) for generating an elastic wave in a target object S; an illumination unit (pulsed laser light source 13 and illumination light lens 14) for performing stroboscopic illumination onto a measurement region of a surface of the target object S; and a displacement measurement unit (speckle shearing interferometer 15) for collectively measuring displacements in a normal direction at each point of the measurement region with respect to at least three mutually-different phases of the elastic wave by controlling a phase of the elastic wave and a timing of the stroboscopic illumination. Defects in the measurement region are detected based on the displacements in the normal direction at each point of the measurement region with respect to at least three phases that are obtained by the displacement measurement unit.

13 Claims, 3 Drawing Sheets

(51) Int. Cl.
*G01M 7/00* (2006.01)
*G01B 17/00* (2006.01)
*G01N 21/17* (2006.01)
*G01N 21/88* (2006.01)
*G01N 29/04* (2006.01)
*G01N 29/24* (2006.01)

(52) U.S. Cl.
CPC .......... *G01B 17/00* (2013.01); *G01M 5/0033* (2013.01); *G01M 5/0066* (2013.01); *G01M 5/0091* (2013.01); *G01M 7/00* (2013.01); *G01N 21/1702* (2013.01); *G01N 21/8806* (2013.01); *G01N 29/043* (2013.01); *G01N 29/045* (2013.01); *G01N 29/2418* (2013.01); *G01N 2021/1706* (2013.01); *G01N 2021/8838* (2013.01); *G01N 2201/0697* (2013.01); *G01N 2201/06113* (2013.01); *G01N 2291/0232* (2013.01); *G01N 2291/0234* (2013.01)

(58) Field of Classification Search
CPC ... G01N 2021/1706; G01N 2021/8838; G01N 2201/0697; G01N 2201/06113
See application file for complete search history.

(56) References Cited

U.S. PATENT DOCUMENTS

| | | |
|---|---|---|
| 5,439,157 A | 8/1995 | Geier et al. |
| 5,546,187 A | 8/1996 | Pepper et al. |
| 6,057,927 A | 5/2000 | Levesque et al. |
| 2003/0057972 A1* | 3/2003 | Pfaff ................ G01R 15/241 324/754.23 |
| 2005/0023434 A1 | 2/2005 | Yacoubian |
| 2007/0157730 A1 | 7/2007 | Ochiai et al. |
| 2007/0234809 A1* | 10/2007 | Klein ................ G01N 21/1702 73/602 |
| 2008/0243441 A1* | 10/2008 | Chen ................ G01B 11/2441 702/190 |
| 2009/0007678 A1 | 1/2009 | Fukutomi et al. |
| 2011/0284508 A1 | 11/2011 | Miura et al. |
| 2012/0300608 A1* | 11/2012 | Masumura ........ G01N 21/4795 369/103 |
| 2013/0329953 A1* | 12/2013 | Schreier ............. G06T 7/2093 382/103 |
| 2015/0148654 A1* | 5/2015 | Whanwook ........... A61B 3/102 600/407 |
| 2016/0265900 A1* | 9/2016 | Yang .................... G01B 11/162 |
| 2017/0176393 A1 | 6/2017 | O'Donnell et al. |
| 2017/0350690 A1 | 12/2017 | Hatahori et al. |

OTHER PUBLICATIONS

Communication dated Oct. 22, 2018 from the United States Patent and Trademark Office in counterpart U.S. Appl. No. 16/004,966.

Yoshiaki Kanno et al., "Measurement of Quartz Crystal Resonator's Vibration by Laser Horographic Interferometer", Bulletin of the Faculty of Engineering, Hokkaido University, 1982, pp. 13-20, No. 109.

Toshinori Nakajima, "Vibration Analysis by Holography", Oyo-Butsuri, 1972, pp. 560-573, vol. 41, No. 6.

* cited by examiner

US 10,267,618 B2

DEFECT DETECTION METHOD AND DEFECT DETECTION APPARATUS

TECHNICAL FIELD

The present invention relates to a method and an apparatus for non-contact detecting defects on a surface of and inside an object such as a concrete or steel structure.

BACKGROUND ART

A laser ultrasound method is one technique for non-contact detecting and measuring defects on a surface of and inside an object such as a concrete or steel structure. In the laser ultrasound method, the surface displacement of a target object is measured by generating an elastic wave in the target object, and meanwhile casting a laser beam at the target object and detecting reflected light with a laser interferometer. Because displacements caused by an elastic wave change discontinuously across defects, defects can be detected by measuring the distribution of the displacements. However, since the detection laser (probe laser) of a laser interferometer is spot-like, it is necessary to move the laser spot across (or scan) the entire inspection region of a target object, and a problem is that such scanning takes time.

As an improvement on the laser ultrasound method, an inspection technique is available which uses electronic speckle pattern interferometry as means for measuring surface displacements caused by an elastic wave (see Patent Literature 1). This method targets an object that has a rough surface. A laser beam is expanded by an expander to generate laser light that is cast onto the entire inspection region of the target object. The laser light is scattered at the rough surface, and the scattered laser lights interfere with each other and generate a light and dark pattern which is called a "speckle pattern". The speckle pattern and reference laser light that was branched from the cast laser light are caused to interfere with each other, and are photographed by a CCD camera or the like. Two such images are taken: one is taken before displacements, and the other is taken after displacements caused by an elastic wave in the object. The distribution of the displacements in the inspection region is then calculated based on the two images. By this means, the displacements in the entire inspection region can be measured at one time.

CITATION LIST

Patent Literature

[Patent Literature 1] JP 2004-101189 A

SUMMARY OF INVENTION

Technical Problem

Two problems exist with respect to the inspection technique that uses electronic speckle pattern interferometry.

The first problem is that because measurement of a speckle pattern is performed only at two time points, namely, before and after generation of an elastic wave, only a single state of a certain phase of the elastic wave is observed. If the wavelength of the elastic wave is small relative to the size of the measurement region, there are a large amplitude portion and a small amplitude portion in the measurement region. Since a displacement at a defect differs depending on the state of the wave there, if a measurement is performed based only on a single state, the result of the defect detection varies depending on the location of the defect in the measurement region.

The second problem is that because there is a large difference between the optical paths of the reflected light and reference light that interfere with each other, the method is susceptible to disturbances such as environmental vibrations. This is a significant problem when a defect detection is done as a regular inspection of a fixed structure or the like, since such inspection is performed on site.

A problem to be solved by the present invention is to provide a defect detection method and apparatus that can inspect a measurement region of a target object at one time and can obtain consistent results within the measurement region.

Solution to Problem

A defect detection method according to the present invention that has been made to solve the above described problem includes:

a) a step of generating an elastic wave in a target object;

b) a step of performing stroboscopic illumination onto a measurement region of a surface of the target object;

c) a step of collectively measuring displacements in a normal direction at each point in the measurement region with respect to at least three mutually-different phases of the elastic wave by controlling a phase of the elastic wave and a timing of the stroboscopic illumination; and d) a step of detecting a defect in the measurement region based on the displacements in the normal direction at each point in the measurement region with respect to the at least three phases.

In a case where a defect exists in a measurement region of a target object (an object under inspection), displacements in the normal direction (front-to-rear direction) at each point in the region change discontinuously at the defect. By this means, a defect within the measurement region can be detected.

According to the defect detection method of the present invention, because a measurement region of a target object can be inspected at one time, inspection can be performed in a short time. Further, by measuring displacements in a normal direction (out-of-plane direction) at each point within a measurement region on the surface of the target object with respect to at least three mutually-different phases of an elastic wave generated in the target object, a complete vibrational state of the elastic wave at all locations in the measurement region can be reproduced regardless of the size of a wavelength (with respect to the measurement region) of the elastic wave, and thus inconsistencies in the defect detection capability that depend on the location within the measurement region do not arise. The complete vibrational state of an elastic wave can be reproduced, for example, by determining a continuous vibration waveform based on measurement data regarding discrete displacements by numerical calculation that applies the method of least squares. Although in a case where a vibration waveform is a sinusoidal wave, the required minimum number of phases in order to determine the vibration waveform by numerical calculation is three, the accuracy of the vibration waveform that is calculated can be improved by making the number of phases for which measurement is performed greater than three.

Further, the sensitivity of defect detection can be improved by detecting harmonic components of an elastic wave generated in the target object. In a case where minute defects are present in a target object, in some cases many harmonic components are included in the aforementioned discontinuous changes that arise at the defects, and hence the detection sensitivity with respect to minute defects can be increased by detecting such harmonic components. In order to detect an $n^{th}$-order harmonic component of an elastic wave generated in a target object, the number of phases for which to perform measurement must be made at least [$2n+1$] (where n is a natural number that is equal to or greater than 2).

Apart from the aforementioned speckle interferometry, speckle shearing interferometry can also be used as a method for collectively measuring displacements in the normal direction at each point in the measurement region. In the case of using speckle shearing interferometry, the defect detection method according to the present invention includes each of the following steps:

a) a step of generating an elastic wave in a target object;

b) a step of performing stroboscopic illumination onto a measurement region of a surface of the target object;

c) a step of collectively measuring displacements in a normal direction at each point in the measurement region with respect to at least three mutually-different phases of the elastic wave using speckle shearing interferometry by controlling a phase of the elastic wave and a timing of the stroboscopic illumination; and d) a step of detecting a defect in the measurement region based on the displacements in the normal direction at each point in the measurement region with respect to the at least three phases.

Speckle shearing interferometry is a method that casts a laser light onto an entire measurement region, causes light beams that are reflected back from two points at positions that deviate from each other in the in-plane direction of the measurement region to interfere with each other, and detects a relative displacement between the two points (a deviation in the normal direction) by determining phases of the interference light. A phase shift method that changes the phases of light from two points into at least three different states can be used as a method for determining the phases of the interference light. Specifically, the light from one of the two points is passed through a phase shifter, and shift amounts of the phase shifter are set to at least three kinds of values. Of course, the lights from the two points may also be passed through the phase shifter and the phases of the two lights may be changed relatively.

According to the defect detection method of the present invention, relative displacements between two adjacent points are measured in this manner over the entire region within a measurement region with respect to at least three mutually-different phases of an elastic wave.

Since two light beams for measuring a displacement at a certain point pass along substantially the same optical path, speckle shearing interferometry can overcome the weak point of the aforementioned conventional electronic speckle interferometry; the method is susceptible to environmental disturbances because the environments through which the measurement light and the reference light pass are different to each other.

A defect detection apparatus according to the present invention for implementing the above described defect detection method includes:

a) a generation unit for generating an elastic wave in a target object;

b) an illumination unit for performing stroboscopic illumination onto a measurement region of a surface of the target object; and c) a displacement measurement unit for collectively measuring displacements in a normal direction at each point in the measurement region with respect to at least three mutually-different phases of the elastic wave by controlling a phase of the elastic wave and a timing of the stroboscopic illumination.

Detection of a defect may be conducted by creating an image based on displacements in the normal direction at each point in the measurement region that were collectively measured with respect to at least three mutually-different phases of the elastic wave that are obtained by the displacement measurement unit (an inspector can carry out detection of defects within the measurement region based on the image), or may be performed by detecting a defect within the measurement region by detecting, for example, discontinuous points by data processing (without creating an image). The image creation or data processing may be performed by providing an image creating unit or a data processing unit in the defect detection apparatus according to the present invention, or may be performed by an external computer.

Further, a defect detection apparatus according to the present invention that uses speckle shearing interferometry includes:

a) a generation unit for generating an elastic wave in a target object;

b) an illumination unit for performing stroboscopic illumination onto a measurement region of a surface of the target object; and c) a displacement measurement unit for collectively measuring displacements in a normal direction at each point in the measurement region with respect to at least three mutually-different phases of the elastic wave using speckle shearing interferometry, by controlling a phase of the elastic wave and a timing of the stroboscopic illumination.

Advantageous Effects of Invention

According to the defect detection method and apparatus of the present invention, because a measurement region of a target object is inspected at one time, inspection can be performed in a short time period. Further, since displacements in the normal direction (out-of-plane direction) at each point in the measurement region on the surface of the target object are measured with respect to at least three mutually-different phases of an elastic wave that is generated in the target object, a complete vibrational state of the elastic wave at all locations in the measurement region can be reproduced regardless of the size of a wavelength (with respect to the measurement region) of the elastic wave, and thus inconsistencies in the defect detection capability that depend on the location within the measurement region do not arise.

DESCRIPTION OF EMBODIMENTS

An embodiment of the defect detection method and defect detection apparatus according to the present invention will now be described using FIG. 1 to FIG. 4A and FIG. 4B.

Figure 1:
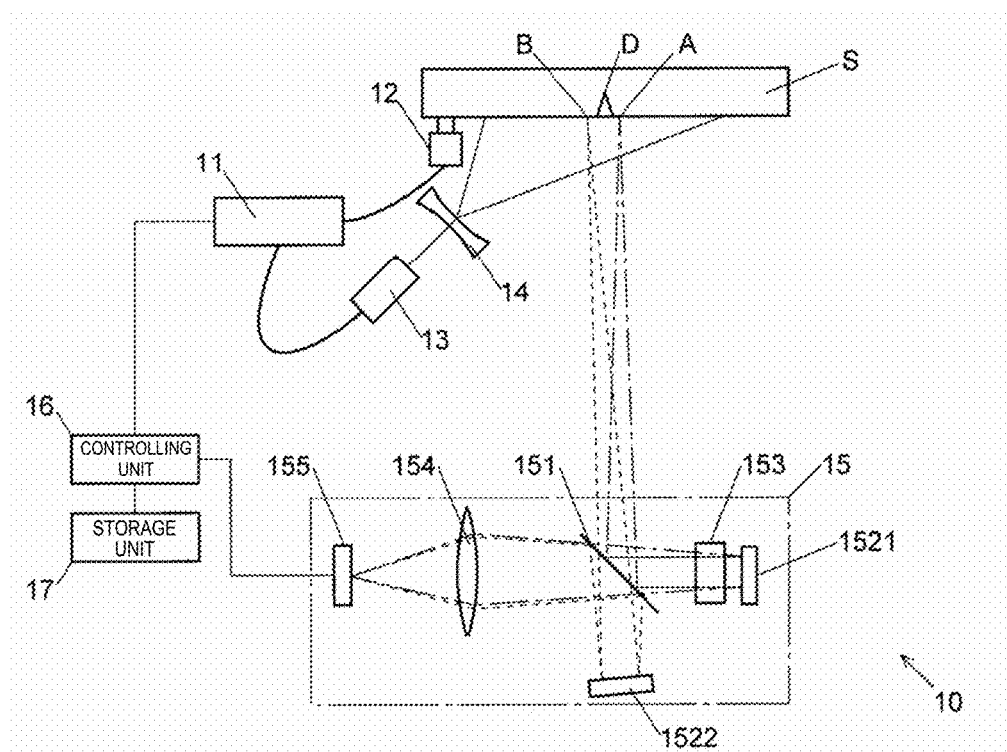
FIG. 1 is a schematic configuration diagram illustrating one embodiment of a defect detection apparatus according to the present invention.

FIG. 1 is a schematic configuration diagram of a defect detection apparatus 10 of the present embodiment. The defect detection apparatus 10 includes a signal generator 11, a vibrator 12, a pulsed laser light source 13, an illumination light lens 14, a speckle shearing interferometer 15, a controlling unit 16 and a storage unit 17.

The signal generator 11 is connected by a cable to the vibrator 12, and generates an alternating current signal and sends the alternating current signal to the vibrator 12. The vibrator 12 is caused to contact against a target object (object under inspection) S and used. The vibrator 12 receives the alternating current signal from the signal generator 11 and converts the signal to mechanical vibrations, and imparts the mechanical vibrations to the target object S. By this means, elastic waves are generated in the target object S. The signal generator 11 and the vibrator 12 correspond to the aforementioned generation unit.

The signal generator 11 is also connected to the pulsed laser light source 13 by a cable that is different from the cable connecting the signal generator 11 to the vibrator 12. The signal generator 11 sends a pulsed electric signal (pulse signal) to the pulsed laser light source 13 at a timing at which the alternating current signal becomes a predetermined phase. The predetermined phase and the timing that is determined based the predetermined phase are changed as described later while performing a defect detection. The pulsed laser light source 13 is a light source that outputs a pulsed laser light upon receiving a pulse signal from the signal generator 11. The illumination light lens 14 is disposed between the pulsed laser light source 13 and the target object S, and is constituted by a concave lens. The illumination light lens 14 serves a function of spreading the pulsed laser light from the pulsed laser light source 13 over the entire measurement region of the surface of the target object S. The pulsed laser light source 13 and the illumination light lens 14 are components that stroboscopically illuminate the measurement region of the surface of the target object S at the aforementioned timing, and correspond to the above described illumination unit.

The speckle shearing interferometer 15 corresponds to the aforementioned displacement measurement unit, and includes a beam splitter 151, a first reflecting mirror 1521, a second reflecting mirror 1522, a phase shifter 153, a condenser lens 154 and an image sensor 155. The beam splitter 151 is a half mirror that is disposed at a position at which illumination light reflected at the measurement region of the surface of the target object S is incident. The first reflecting mirror 1521 is disposed on the optical path of illumination light reflected at the beam splitter 151. The second reflecting mirror 1522 is disposed on the optical path of illumination light passed through the beam splitter 151. The phase shifter 153 is disposed between the beam splitter 151 and the first reflecting mirror 1521, and changes (shifts) the phase of light passing through the phase shifter 153. The image sensor 155 is disposed on an optical path of illumination light that, after being reflected at the beam splitter 151, is reflected at the first reflecting mirror 1521 and passes through the beam splitter 151, and an optical path of illumination light that, after passing through the beam splitter 151, is reflected at the second reflecting mirror 1522 and is thereafter reflected at the beam splitter 151. The condenser lens 154 is disposed between the beam splitter 151 and the image sensor 155.

The first reflecting mirror 1521 is disposed so that the reflective surface thereof is at an angle of 45° with respect to the reflective surface of the beam splitter 151. In contrast, the second reflecting mirror 1522 is disposed so that the reflective surface thereof is at a slightly inclined angle from 45° relative to the reflective surface of the beam splitter 151. By disposing the first reflecting mirror 1521 and the second reflecting mirror 1522 in this manner, at the image sensor 155, irradiation light (indicated by an alternate long and short dashed line in FIG. 1) reflected at a point A on the surface of the target object S and at the first reflecting mirror 1521, and irradiation light (indicated by a broken line in FIG. 1) reflected at a point B located at a position that deviates slightly from the point A on the aforementioned surface and is also reflected at the second reflecting mirror 1522 are incident at the same position on the image sensor 155 and interfere with each other. The image sensor 155 has a large number of detecting elements, and light from a large number of points (the aforementioned points A) on the surface of the target object S is incident on the image sensor 155 via the first reflecting mirror 1521 and the phase shifter 153 and is detected by respective individual detecting elements. Similarly, with respect to the points B also, light from a large number of points is incident on the image sensor 155 via the second reflecting mirror 1522 and is detected by the respective individual detecting elements.

The controlling unit 16 controls the signal generator 11 and also performs data processing based on detection signals obtained from the respective detecting elements of the image sensor 155. The storage unit 17 stores detection signals obtained from each of the detecting elements of the image sensor 155, and data that after the processing by the controlling unit 16.

Figure 2:
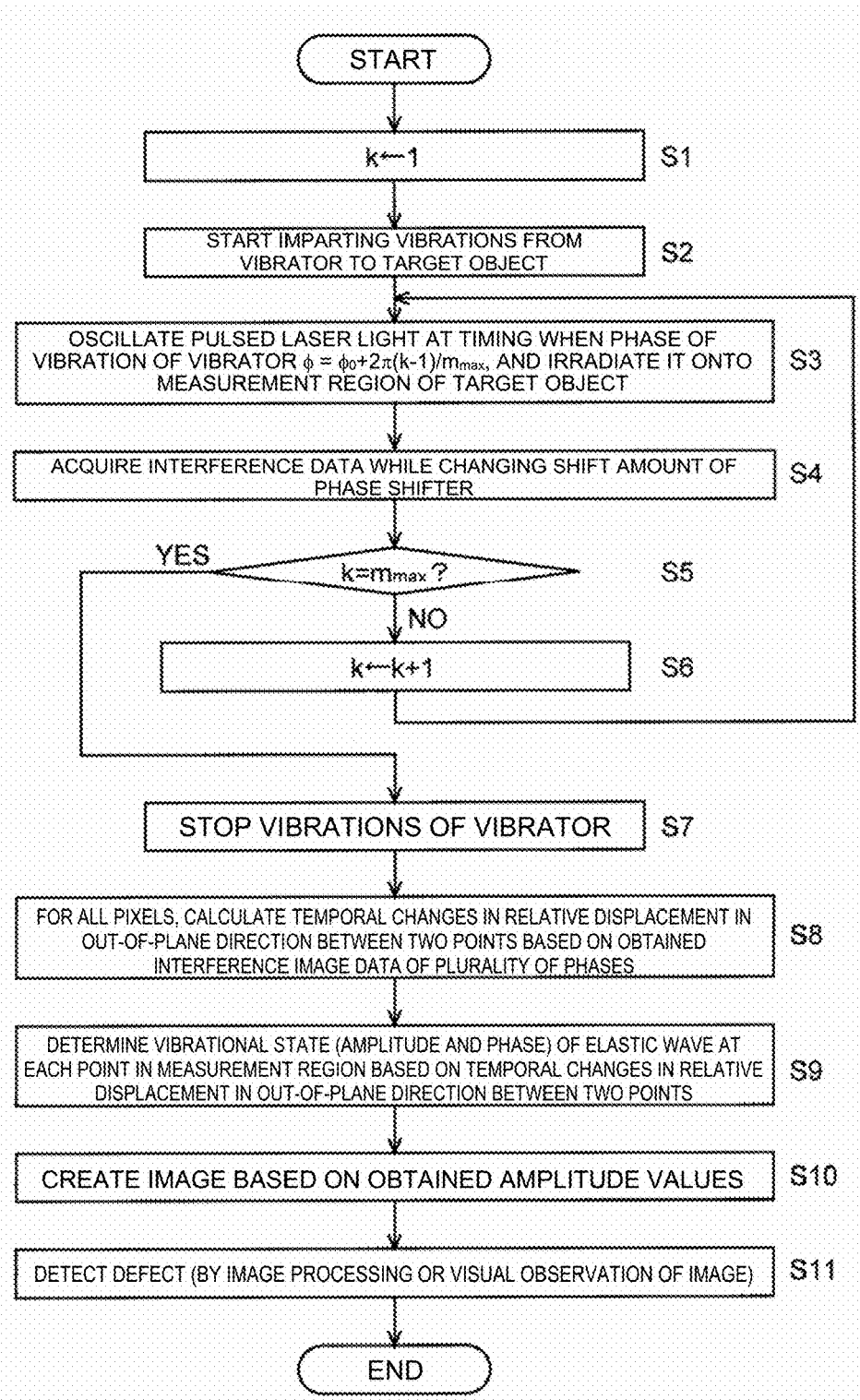
FIG. 2 is a flowchart illustrating one embodiment of a defect detection method according to the present invention.

Hereunder, operations of the defect detection apparatus 10 as one embodiment of the defect detection method according to the present invention will be described using the flowchart in FIG. 2 and the graphs in FIGS. 3A, 3B and 3C. In the present embodiment, measurement of surface displacement is performed $m_{max}$ times, where $m_{max} \geq 3$, in which the respective phases of vibrations of the vibrator 12 are different. Here, the term "phases of vibrations of the vibrator 12" refers to respective phases of the alternating current signal sent from the signal generator 11 to the vibrator 12, and corresponds to a phase at a point where the vibrator 12 contacts of an elastic wave generated in the target object S. Hereunder, each measurement of the surface displacement is represented by "$k^{th}$ measurement" using a numerical value k (any natural number between 1 and $m_{max}$). Further, in the following description, first, all of the steps are described with respect to a case where $m_{max}=3$ as the simplest example, and thereafter a case is described in which $m_{max}$ is a larger number.

First, the initial value of k is set to 1 (step S1), and by sending an alternating current signal to the vibrator 12 from the signal generator 11, imparting of vibrations to the target object S from the vibrator 12 is started (step S2). By this means, an elastic wave is generated in the target object S.

Next, at each timing at which a phase of a vibration of the vibrator 12 is represented by $[\phi_0 + 2\pi(k-1)/m_{max}]$ using a predetermined initial value $\phi_0$ (for example, $\phi_0=0$), the signal generator 11 sends a pulse signal to the pulsed laser light source 13. Since k=1 at this stage, the phase of a vibration by the vibrator 12 when the pulse signal is sent is $\phi_0$. The pulsed laser light source 13 repeatedly outputs illumination light that is pulsed laser light every time the pulsed laser light source 13 receives a pulse signal. The diameter of the illumination light is expanded by the illumination light lens 14, and the illumination light is cast onto the entire measurement region of the surface of the target object S (step S3).

Illumination light is reflected at the surface of the target object S and is incident on the beam splitter 151 of the speckle shearing interferometer 15. A part of the illumination light is reflected by the beam splitter 151, passes through the phase shifter 153 and is thereafter reflected by the first reflecting mirror 1521, and after passing through the phase shifter 153 once more, a part of the illumination light passes through the beam splitter 151 and is incident on the image sensor 155. The remainder of the illumination light that is incident on the beam splitter 151 passes through the beam splitter 151 and is reflected at the second reflecting mirror 1522, and a part thereof is then reflected at the beam splitter 151 and is incident on the image sensor 155. As described above, at the image sensor 155, irradiation light that is reflected at a large number of points on the surface of the target object S is detected by the respective individual detecting elements.

While the illumination light that is pulsed laser light is being repeatedly output, the phase shifter 153 changes (shifts) the phase of irradiation light (that is, irradiation light reflected at the point A) that passes through the phase shifter 153. By this means, a phase difference between irradiation light reflected at the point A and irradiation light reflected at the point B changes, and while the phase difference is changed, the respective detecting elements of the image sensor 155 detect the intensity of interference light as a result of interference of these two irradiation lights (step S4). FIG. 3A shows a graph of an example of a relation between a shift amount of a phase that is shifted by the phase shifter 153 and the intensity of interference light that is detected by the detecting elements of the image sensor 155, which is obtained when the phase of a vibration of the vibrator 12 is $\phi_0$. Although a relation in which the detected intensity changes in a sinusoidal wave shape relative to the phase shift amount is illustrated by a continuous curve in FIGS. 3A, 3B and 3C, the data that is actually measured is discrete data and the sinusoidal waveform is reproduced by a least squares method based on the measured data. Therefore, it is necessary to detect the intensity using at least three different phase shift amounts.

Next, in step S5, it is determined whether or not the value of k reached $m_{max}$. Because k is still equal to 1 at this stage and has not reached $m_{max}$ (which is 3 in this example), the result of the determination in step S5 is "No". When the result determined in step S5 is "No", the processing proceeds to step S6 and the value of k is incremented by 1 to "2" (the processing when the result determined in step S5 is "Yes" is described later).

Next, the processing returns to step S3, the signal generator 11 sends a pulse signal to the pulsed laser light source 13 at each timing when the phase of the vibration of the vibrator 12 is k=2 in $[\phi_0+2\pi(k-1)/m_{max}]$, that is, $[\phi_0+2\pi/3] \equiv \phi_1$, and the pulsed laser light source 13 repeatedly casts illumination light that is pulsed laser light onto the surface of the target object S at the timings of receiving the pulse signal. Subsequently, while changing (shifting) the phase of irradiation light reflected at the point A to at least three values by means of the phase shifter 153, the respective detecting elements of the image sensor 155 detect the intensity of interference light arose by the irradiation light reflected at point A and passed through the phase shifter 153 and other components and the irradiation light reflected at the point B (step S4).

Figure 3A:
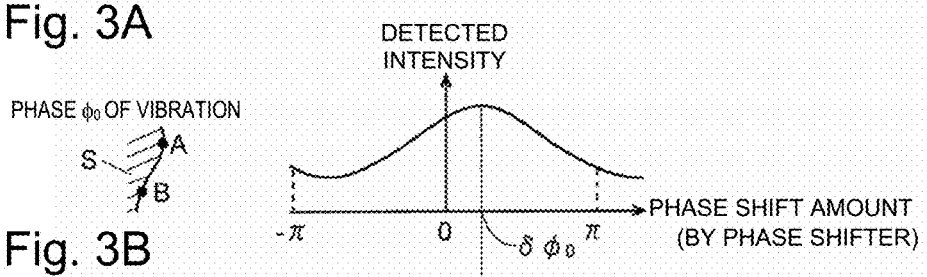
FIGS. 3A, 3B and 3C are graphs for describing the principles of the defect detection method of the present embodiment.
Figure 3B:
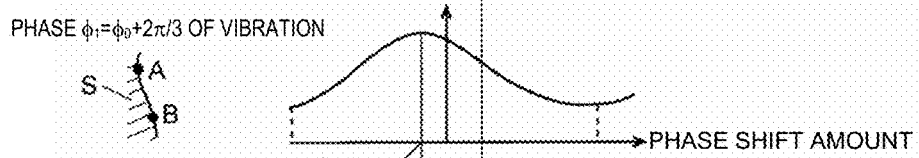

FIG. 3B shows a graph of a relation between a shift amount of a phase that is shifted by the phase shifter 153 and the intensity of interference light that is detected by the detecting elements of the image sensor 155, which is obtained when the phase of a vibration of the vibrator 12 is $\phi_1$. Comparing FIG. 3B and the aforementioned FIG. 3A, it is found that the peak position of the intensity of the interference light deviates by $\delta\phi_1-\delta\phi_0$ between the two drawings. This deviation indicates that a phase difference between the optical path from the point A and the optical path from the point B changed due to a difference in the phase of the vibration by the vibrator 12 at the time of detection. This change in the phase difference between the optical paths indicates that the relative displacement in the out-of-plane direction between point A and point B is changed.

After the operation in step S4 is executed with respect to k=2 in this manner, since k has not yet reached $m_{max}$ (=3), "No" is determined as the result in step S5, and the value of k is incremented by 1 to "3" in step S6. Thereafter, the processing returns to step S3, the pulsed laser light source 13 repeatedly casts illumination light that is pulsed laser light onto the surface of the target object S at each timing when the phase of the vibration of the vibrator 12 is k=3 in $[\phi_0+2\pi(k-1)/m_{max}]$, that is, $[\phi_0+4\pi/3] \equiv \phi_2$, and the respective detecting elements of the image sensor 155 detect the intensity of the interference light (step S4). Thus, as shown in FIG. 3C, a relation between the shift amount of the phase that is shifted by the phase shifter 153 and the intensity of interference light when the phase of the alternating current signal is $\phi_2$ is obtained.

Thereafter, since the value of k is 3 and k has therefore reached $m_{max}$, "Yes" is determined as the result in step S5 and the processing proceeds to step S7. In step S7, sending of an alternating current signal from the signal generator 11 to the vibrator 12 is stopped, and consequently the vibrator 12 stops vibrating.

Next, in step S8 and S9, the vibrational state (amplitude and phase) of the elastic wave at each point in the measurement region is determined by the following operations.

Figure 3C:
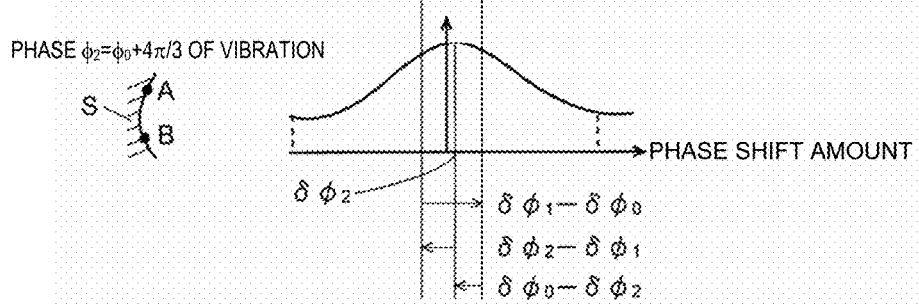

First, for each detecting element of the image sensor 155, maximum output phase shift amounts $\delta\phi_0$, $\delta\phi_1$ and $\delta\phi_2$ at which the output of the detecting element becomes a maximum at the respective phases $\phi_0$, $\phi_1$ and $\phi_2$ of each vibration while the shift amounts of the phases are changed by the phase shifter 153 are determined (see the graphs in FIG. 3A to FIG. 3C). In addition, the differences $(\delta\phi_1-\delta\phi_0)$, $(\delta\phi_2-\delta\phi_1)$ and $(\delta\phi_0-\delta\phi_2)$ between the maximum output phase shift amounts when the phases of the vibration are different are determined (step S8). These three differences between the maximum output phase shift amounts show three sets of relative displacements in the out-of-plane direction between point A and point B with two data sets for which the respective phases of the vibration of the vibrator 12 are different (that is, the time is different). Based on these three sets of relative displacements, the values of three parameters, namely, the amplitude of the vibration, the phase of the vibration, and a central value (DC component) of the vibration are obtained at each point in the measurement region (step S9).

An image is created based on the values of the amplitude and phase of the vibration at each point which are obtained in this manner (step S10). For example, by increasing the brightness of a pixel corresponding to a measurement point as the amplitude at the measurement point is larger, differences in the amplitude of a vibration can be represented by the contrast of an image.

By performing processing using known image processing technique on an image created in the above manner, a defect D on the surface of the target object S is detected (step S11). For example, when a position on the image is moved, a location at which the contrast of pixels changes sharply is detected as a defect. Instead of detecting defects by image processing, an inspector may visually observe the image to detect a defect. Alternatively, a configuration may be adopted in which an image is not created, and for example, a defect in the measurement region is detected by detecting discontinuous points or the like. All the operations of the defect detection apparatus 10 and the steps of the defect detection method end upon the end of the processing in step S11.

Figure 4A:
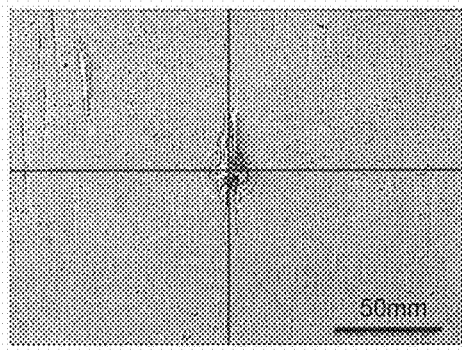
FIG. 4A is a photograph obtained by photographing a surface of a target object that was taken as the subject of a defect detection.
Figure 4B:
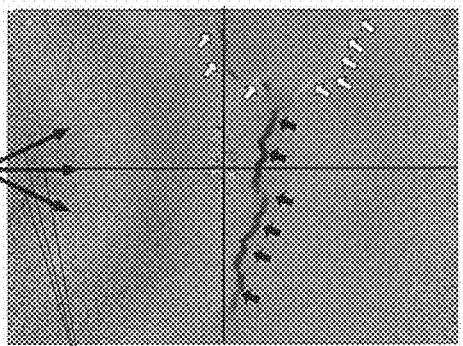
FIG. 4B is an image that was obtained by the defect detection method and apparatus of the present embodiment.

FIG. 4A and FIG. 4B illustrate an example in which the surface of a target object that consists of a concrete wall was inspected using the defect detection method and apparatus of the present embodiment. FIG. 4A is a photograph of the surface of the target object photographed with a typical camera. FIG. 4B is an image obtained using the defect detection method and apparatus of the present embodiment. Although defects such as cracks cannot be found in FIG. 4A, defects such as cracks can be found at the positions indicated by black arrows and white arrows in FIG. 4B. Among these defects, the defects indicated by the black arrows cannot be identified by visual observation such as in the photograph shown in FIG. 4A, but can be identified by visual observation if a specialist enlarges the defects using a magnifier. In contrast, the defects indicated by the white arrows cannot be identified by visual observation even if the specialist enlarges the defects using the magnifier, but can be identified only using the method and apparatus of the present embodiment.

The present invention is not limited to the above described embodiment.

In the above described example, although $m_{max}$ is taken as being equal to 3, by choosing a number for $m_{max}$ that is larger than a number represented by [2n+1] (n is a natural number equal to or greater than 2), it is possible to detect up to the $n^{th}$-order component ($n^{th}$ harmonic component) of an elastic wave generated in the target object S. That is, because (2n+1) sets or more of relative displacements in the out-of-plane direction between the point A and the point B are obtained, the values of (2n+1) parameters, namely, the amplitude of a fundamental wave, the phase of the fundamental wave, the amplitude of the second harmonic, the phase of the second harmonic . . . the amplitude of the $n^{th}$ harmonic, the phase of the $n^{th}$ harmonic and the DC component of the elastic wave are obtained.

Further, although in the above described embodiment the signal generator 11 and vibrator 12, and the signal generator 11 and the pulsed laser light source 13 are connected with cables (wired connections), these components may be wirelessly connected. In particular, it is preferable for the signal generator 11 and the vibrator 12 to be wirelessly connected. By wirelessly connecting the signal generator 11 and the vibrator 12, after the vibrator 12 is brought into contact with the target object S, even if constituent elements of the defect detection apparatus 10 other than the vibrator 12 is disposed separate from the target object S, it is not necessary to prepare a long cable. Such a configuration that uses a wireless connection is useful in a case of inspecting, for example, a large-scale object under inspection S such as a bridge or other infrastructure.

Although in the above embodiment the vibrator 12 that contacts with the surface of the target object S is employed, a powerful speaker or the like that is placed in a non-contact state with the surface of the target object S may be employed as a vibrator instead of the vibrator 12.

A window or various kinds of optical filters may be disposed on an optical path in which reflected light from the target object S enters the image sensor in the above embodiment for the purpose of protecting optical components or improving the signal-to-noise ratio of the apparatus or the like. Examples of the various kinds of optical filters include a polarizing plate, a wave plate, a band-pass filter, a short-pass filter and a long-pass filter.

Although in the above embodiment the condenser lens 154 is disposed between the beam splitter 151 and the image sensor 155, the arrangement is not limited thereto. Further, the condenser lens 154 may be constituted by a plurality of lens or a plurality of lens groups. For example, a configuration can be adopted in which the condenser lens 154 is constituted by a lens group 1 and a lens group 2, and the lens group 1 is disposed between the target object S and the beam splitter 151, and the lens group 2 is disposed between the beam splitter 151 and the image sensor 155. At such time, by adopting a configuration in which the lens group 1 can be detached and attached without disassembling a housing of the speckle shearing interferometer 15, the angle of view can be easily changed by exchanging the lens group 1 for another lens group having a different focal length. By this means, for example, by adjusting the angle of view in accordance with the distance between the target object S and the speckle shearing interferometer 15 and setting an appropriate measurement region size, detection for defects can be realized with respect to a target object existing in various places. Examples of lenses that can be used for the lens group 1 include a telephoto lens, a wide-angle lens, a macro lens and a zoom lens.

REFERENCE SIGNS LIST

10 . . . Defect Detection Apparatus
11 . . . Signal Generator
12 . . . Vibrator
13 . . . Pulsed Laser Light Source
14 . . . Illumination Light Lens
15 . . . Speckle Shearing Interferometer
151 . . . Beam Splitter
1521 . . . First Reflecting Mirror
1522 . . . Second Reflecting Mirror
153 . . . Phase Shifter
154 . . . Condenser Lens
155 . . . Image Sensor
16 . . . Controlling Unit
17 . . . Storage Unit
D . . . Defect
S . . . Target Object

The invention claimed is:
1. A defect detection method, comprising:
   a) a step of generating an elastic wave in a target object;
   b) a step of performing stroboscopic illumination onto a measurement region of a surface of the target object;
   c) a step of collectively measuring displacements in a normal direction at each point in the measurement region with respect to at least three mutually-different phases of the elastic wave by controlling a phase of the elastic wave and a timing of the stroboscopic illumination; and d) a step of detecting a defect in the measurement region based on the displacements in the normal direction at each point in the measurement region with respect to the at least three phases.

2. The defect detection method according to claim 1, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and the defect in the measurement region is detected based on the $n^{th}$-order harmonic component.

3. The defect detection method according to claim 1, wherein the step of collectively measuring displacements in the normal direction at each point in the measurement region is performed using speckle shearing interferometry.

4. The defect detection method according to claim 3, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and the defect in the measurement region is detected based on the $n^{th}$-order harmonic component.

5. A defect detection apparatus, comprising:
a) a generation unit configured to generate an elastic wave in a target object;
b) an illumination unit configured to perform stroboscopic illumination onto a measurement region of a surface of the target object; and
c) a displacement measurement unit configured to collectively measure displacements in a normal direction at each point in the measurement region with respect to at least three mutually-different phases of the elastic wave by controlling a phase of the elastic wave and a timing of the stroboscopic illumination.

6. The defect detection apparatus according to claim 5, wherein the displacement measurement unit collectively measures the displacements in the normal direction at each point in the measurement region using speckle shearing interferometry.

7. The defect detection apparatus according to claim 6, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and a defect in the measurement region is detected based on the $n^{th}$-order harmonic component.

8. The defect detection apparatus according to claim 5, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and a defect in the measurement region is detected based on the $n^{th}$-order harmonic component.

9. A defect detection apparatus, comprising:
a) a generation unit comprising a signal generator and a vibrator, the generation unit configured to generate, with the signal generator and the vibrator, an elastic wave in a target object;
b) a light source configured to perform stroboscopic illumination onto a measurement region of a surface of the target object; and
c) an interferometer configured to collectively measure displacements in a normal direction at each point in the measurement region with respect to at least three mutually-different phases of the elastic wave by controlling a phase of the elastic wave and a timing of the stroboscopic illumination.

10. The defect detection apparatus according to claim 9, wherein the interferometer collectively measures the displacements in the normal direction at each point in the measurement region using speckle shearing interferometry.

11. The defect detection apparatus according to claim 10, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and a defect in the measurement region is detected based on the $n^{th}$-order harmonic component.

12. The defect detection apparatus according to claim 9, wherein a number of phase states with respect to the at least three phases is equal to or greater than (2n+1), where the n is a natural number equal to or greater than 2, and an $n^{th}$-order harmonic component of the elastic wave is detected based on the displacements in the normal direction at each point in the measurement region, and a defect in the measurement region is detected based on the $n^{th}$-order harmonic component.

13. The defect detection apparatus according to claim 9, wherein the generation unit is configured to generate, with the signal generator and the vibrator, the elastic wave in the target object while the vibrator is in a non-contact state with the target object.

* * * * *